United States Patent [19]

Hamada et al.

[11] Patent Number: 5,907,052
[45] Date of Patent: May 25, 1999

[54] PROCESS FOR PRODUCING ACRYLONITRILE OR METHACRYLONITRILE FROM PROPANE OR ISOBUTANE BY AMMOXIDATION

[75] Inventors: Kazuyuki Hamada, Kurashiki; Satoru Komada, Yokohama, both of Japan

[73] Assignee: Asahi Kasei Kogyo Kabushiki Kaisha, Osaka, Japan

[21] Appl. No.: 09/132,224

[22] Filed: Aug. 11, 1998

[30] Foreign Application Priority Data

Aug. 11, 1997 [JP] Japan ................................. 9-227000
Aug. 11, 1997 [JP] Japan ................................. 9-227001

[51] Int. Cl.⁶ ................................................ C07C 253/00
[52] U.S. Cl. ........................ 558/320; 558/321; 558/322; 558/323
[58] Field of Search ................... 558/320, 321, 558/322, 323

[56] References Cited

U.S. PATENT DOCUMENTS

| | | | |
|---|---|---|---|
| 3,882,159 | 5/1975 | Callahan et al. | 558/319 |
| 4,709,070 | 11/1987 | Sasaki et al. | 558/322 |
| 5,049,692 | 9/1991 | Hatano et al. | 558/319 |
| 5,079,207 | 1/1992 | KBrazdil et al. | 502/205 |
| 5,171,876 | 12/1992 | Suresh et al. | 558/319 |
| 5,231,214 | 7/1993 | Ushikubo et al. | 558/319 |
| 5,422,328 | 6/1995 | Ushikubo et al. | 502/312 |
| 5,446,857 | 11/1995 | Relling et al. | 558/319 |
| 5,801,266 | 9/1998 | Ishii | 558/320 |

FOREIGN PATENT DOCUMENTS

| | | |
|---|---|---|
| 0337028A1 | 10/1989 | European Pat. Off. . |
| 0529853B1 | 3/1993 | European Pat. Off. . |
| 2264403 | 7/1973 | Germany . |
| 3 311521C1 | 1/1984 | Germany . |
| 1-41135 | 9/1989 | Japan . |
| 6-228073 | 8/1994 | Japan . |
| 7-144132 | 6/1995 | Japan . |
| 7-215926 | 8/1995 | Japan . |
| 7-232071 | 9/1995 | Japan . |
| 7-289907 | 11/1995 | Japan . |
| 7-315842 | 12/1995 | Japan . |
| 8-57319 | 3/1996 | Japan . |
| 8-141401 | 6/1996 | Japan . |
| WO 9733863 | 9/1997 | WIPO . |

*Primary Examiner*—Deborah C. Lambkin
*Assistant Examiner*—Joseph Murray
*Attorney, Agent, or Firm*—Birch, Stewart, Kolasch & Birch, LLP

[57] ABSTRACT

A process for producing acrylonitrile or methacrylonitrile from propane or isobutane by ammoxidation, which comprises reacting propane or isobutane with ammonia and molecular oxygen in the gaseous phase in a fluidized-bed reactor containing a catalyst comprising a compound oxide and a silica carrier having supported thereon the compound oxide, wherein the compound oxide contains molybdenum (Mo), tellurium (Te), vanadium (V) and niobium (Nb), and wherein the reaction is performed with an addition of a catalyst activator comprising at least one tellurium compound and optionally at least one molybdenum compound into the reactor. The process of the present invention is advantageous in that the catalytic activity of the catalyst is surely maintained at a high level even without replacing the catalyst with a fresh one by interrupting the ammoxidation reaction, so that production of acrylonitrile or methacrylonitrile by the ammoxidation of propane or isobutane can be stably performed for a prolonged period of time while maintaining a high yield of acrylonitrile or methacrylonitrile.

5 Claims, No Drawings

PROCESS FOR PRODUCING ACRYLONITRILE OR METHACRYLONITRILE FROM PROPANE OR ISOBUTANE BY AMMOXIDATION

BACKGROUND OF THE INVENTION

1. Field of the Invention

The present invention relates to an improved process for producing acrylonitrile or methacrylonitrile from propane or isobutane by ammoxidation. More particularly, the present invention is concerned with a process for producing acrylonitrile or methacrylonitrile from propane or isobutane by ammoxidation, which comprises reacting propane or isobutane with ammonia and molecular oxygen in the gaseous phase in a fluidized-bed reactor containing a catalyst comprising a compound oxide and a silica carrier having supported thereon the compound oxide, wherein the compound oxide contains molybdenum (Mo), tellurium (Te), vanadium (V) and niobium (Nb), and wherein the reaction is performed with an addition of a catalyst activator comprising at least one tellurium compound and optionally at least one molybdenum compound into the reactor. The process of the present invention is advantageous in that the catalytic activity of the catalyst is surely maintained at a high level even without replacing the catalyst with a fresh one by interrupting the ammoxidation reaction, so that production of acrylonitrile or methacrylonitrile by the ammoxidation of propane or isobutane can be stably performed for a prolonged period of time while maintaining a high yield of acrylonitrile or methacrylonitrile.

PRIOR ART

There has been a well-known process for producing acrylonitrile or methacrylonitrile by ammoxidation of propylene or isobutylene. Recently, as a substitute for such a process using propylene or isobutylene, attention has been attracted to a process for producing acrylonitrile or methacrylonitrile by a gaseous phase catalytic ammoxidation of propane or isobutane, i.e., by a gaseous phase catalytic reaction of propane or isobutane with ammonia and molecular oxygen. Further, a number of proposals have been made with respect to catalysts for use in the ammoxidation of propane or isobutane. As these catalysts, especially, oxide catalysts comprising tellurium are attracting attention.

For example, as a catalyst for use in producing acrylonitrile or methacrylonitrile by an ammoxidation of propane or isobutane, oxide catalysts containing molybdenum, tellurium, vanadium and niobium are known. Such oxide catalysts are disclosed in U.S. Pat. Nos. 5,049,692, 5,231,214, 5,422,328, European Patent Publication No. 529 853 B1, Unexamined Japanese Patent Application Laid-Open Specification Nos. 7-144132, 7-232071, 7-289907, 7-315842, 8-57319 and 8-141401.

As further examples of oxide catalysts for use in the gaseous phase catalytic ammoxidation of propane or isobutane, an oxide catalyst containing molybdenum and tellurium is disclosed in Unexamined Japanese Patent Application Laid-Open Specification No. 7-215926; an oxide catalyst containing molybdenum, tellurium and chromium is disclosed in U.S. Pat. No. 5,171,876; an oxide catalyst containing tungsten, tellurium and vanadium is disclosed in Unexamined Japanese Patent Application Laid-Open Specification No. 6-228073; and an oxide catalyst containing vanadium, antimony and tellurium is disclosed in each of U.S. Pat. No. 5,079,207 and European Patent Publication No. 337 028 A1.

However, the tellurium-containing oxide catalysts disclosed in the above patent documents are disadvantageous in that the catalytic activity deteriorates with a lapse of time during the course of the ammoxidation, thus causing a lowering of the yield of the desired unsaturated nitrile, i.e., acrylonitrile or methacrylonitrile.

On the other hand, there have been known methods for activating a deteriorated catalyst by means of a substance capable of restoring the catalytic activity of the deteriorated catalyst (such a substance is hereinafter, frequently referred to as an "activator").

For example, each of U.S. Pat. No. 4,709,070 and Examined Japanese Patent Application Publication No. 1-41135 discloses a method for performing oxidation, ammoxidation or oxidative dehydrogenation of an organic compound in the presence of a tellurium-containing oxide catalyst, wherein a tellurium compound or a combination of a tellurium compound and a molybdenum compound is added, as a catalyst activator, to the reaction system, to thereby maintain the catalytic activity of the catalyst during the reaction. However, the working examples of these patent documents disclose only an ammoxidation of methanol, an ammoxidation of propylene, an ammoxidation of toluene and an oxidative dehydrogenation of butene. None of these documents contain a description about a method for the ammoxidation of propane or isobutane in the presence of an oxide catalyst containing molybdenum, tellurium, vanadium and niobium.

Each of U.S. Pat. 3,882,159, German Patent No. 3,331,521 and International Patent Application Publication No. WO97/33863 discloses a process for producing acrylonitrile or methacrylonitrile by a gaseous phase ammoxidation of propylene or isobutylene in the presence of an oxide catalyst containing molybdenum, wherein the ammoxidation is performed with an addition, into the reaction system, of a molybdenum compound as an activator for the catalyst. However, none of these patent documents describe the use of a tellurium-containing oxide catalyst in producing acrylonitrile or methacrylonitrile from propane or isobutane by ammoxidation.

As apparent from the above, no method has been known for solving the above-mentioned problem arising when a tellurium-containing oxide catalyst is used for producing acrylonitrile or methacrylonitrile by a gaseous phase ammoxidation of propane or isobutane, i.e., the problem of a lowering of the yield of acrylonitrile or methacrylonitrile due to the occurrence of a deterioration of the oxide catalyst with a lapse of time during the course of the ammoxidation.

SUMMARY OF THE INVENTION

In this situation, the present inventors have made extensive and intensive studies with a view toward developing an improved process for producing acrylonitrile or methacrylonitrile from propane or isobutane by ammoxidation, which can solve the above problem accompanying the prior art, thus enabling production of acrylonitrile or methacrylonitrile by the ammoxidation of propane or isobutane to be stably performed for a prolonged period of time while maintaining a high yield of acrylonitrile or methacrylonitrile. As a result, it has unexpectedly been found that, in a process for producing acrylonitrile or methacrylonitrile from propane or isobutane by ammoxidation, which comprises reacting propane or isobutane with ammonia and molecular oxygen in the gaseous phase in a fluidized-bed reactor containing a catalyst comprising a compound oxide and a silica carrier having supported thereon the compound oxide, wherein the compound oxide contains molybdenum (Mo), tellurium (Te), vanadium (V) and niobium (Nb), the above objective can be attained by performing the reaction with an addition of a catalyst activator comprising at least one tellurium compound and optionally at least one molybdenum compound into the reactor. The present invention has been completed, based on this novel finding.

It is, therefore, a primary object of the present invention to provide a process for producing acrylonitrile or methacrylonitrile from propane or isobutane by ammoxidation, which has an advantage in that the catalytic activity of the catalyst is surely maintained at a high level even without replacing the catalyst with a fresh one by interrupting the ammoxidation reaction, so that production of acrylonitrile or methacrylonitrile by the ammoxidation of propane or isobutane can be stably performed for a prolonged period of time while maintaining a high yield of acrylonitrile or methacrylonitrile.

The foregoing and other objects, features and advantages of the present invention will be apparent to those skilled in the art from the following detailed description taken in connection with the appended claims.

DETAILED DESCRIPTION OF THE INVENTION

In the present invention, there is provided a process for producing acrylonitrile or methacrylonitrile from propane or isobutane by ammoxidation, which comprises:

reacting propane or isobutane with ammonia and molecular oxygen in the gaseous phase in a fluidized-bed reactor containing a catalyst comprising a compound oxide and a silica carrier having supported thereon the compound oxide, the compound oxide containing molybdenum (Mo), tellurium (Te), vanadium (V) and niobium (Nb), wherein the reaction is performed with an addition of an activator for the catalyst into the reactor, the activator comprising at least one tellurium compound and optionally at least one molybdenum compound.

For easy understanding of the present invention, the essential features and various preferred embodiments of the present invention are enumerated below.

1. A process for producing acrylonitrile or methacrylonitrile from propane or isobutane by ammoxidation, which comprises:

reacting propane or isobutane with ammonia and molecular oxygen in the gaseous phase in a fluidized-bed reactor containing a catalyst comprising a compound oxide and a silica carrier having supported thereon the compound oxide, the compound oxide containing molybdenum (Mo), tellurium (Te), vanadium (V) and niobium (Nb), wherein the reaction is performed with an addition of an activator for the catalyst into the reactor, the activator comprising at least one tellurium compound and optionally at least one molybdenum compound.

2. The process according to item 1 above, wherein the silica carrier is present in an amount of from 10 to 60% by weight, based on the total weight of the compound oxide and the silica carrier, and wherein the compound oxide is represented by the following formula (1):

$$Mo_1Te_aV_bNb_cX_dO_n \qquad (1)$$

wherein:

X is at least one element selected from the group consisting of tantalum, tungsten, chromium, titanium, zirconium, antimony, bismuth, tin, hafnium, manganese, iron, ruthenium, cobalt, rhodium, nickel, palladium, platinum, zinc, aluminum, gallium, indium, thallium, phosphorus and alkaline earth metals; and a, b, c, d and n are, respectively, the atomic ratios of tellurium, vanadium, niobium, X and oxygen, relative to molybdenum, wherein $0.01 \leq a \leq 1.0$;

$0.1 \leq b \leq 1.0$;

$0.01 \leq c \leq 1.0$;

$0 \leq d \leq 1.0$; and n is a number determined by and consistent with the valence requirements of the other elements present in the compound oxide of formula (1).

3. The process according to item 1 or 2 above, wherein the at least one tellurium compound is selected from the group consisting of metallic tellurium, an inorganic tellurium compound and an organic tellurium compound, and the at least one molybdenum compound is selected from the group consisting of ammonium heptamolybdate, molybdic acid, molybdenum dioxide and molybdenum trioxide.

4. The process according to item 3 above, wherein the inorganic tellurium compound is at least one member selected from the group consisting of telluric acid, tellurium dioxide and tellurium trioxide, and the organic tellurium compound is at least one member selected from the group consisting of methyltellurol and dimethyl telluroxide.

5. The process according to item 1 or 2 above, wherein the at least one tellurium compound is telluric acid and the at least one molybdenum compound is ammonium heptamolybdate.

Hereinbelow, the present invention will be described in more detail.

In the process of the present invention for producing acrylonitrile or methacrylonitrile from propane or isobutane by ammoxidation, propane or isobutane is reacted with ammonia and molecular oxygen in the gaseous phase in a fluidized-bed reactor containing a catalyst comprising a compound oxide and a silica carrier having supported thereon the compound oxide, wherein the reaction is performed with an addition of an activator for the catalyst into the reactor.

The above-mentioned compound oxide contained in the catalyst used in the process of the present invention contains molybdenum (Mo), tellurium (Te), vanadium (V) and niobium (Nb).

In the process of the present invention, the addition of the above-mentioned activator is particularly important to achieve excellent effects of the present invention. Specifically, in the process of the present invention, by the addition of the activator, the catalyst, which has been deteriorated during the ammoxidation, can be easily reactivated. Therefore, the production of (meth)acrylonitrile by the ammoxidation of propane or isobutane can be stably performed for a prolonged period of time while maintaining a high yield of (meth)acrylonitrile.

On the other hand, if an ammoxidation of propane or isobutane is performed in the presence of a catalyst as defined in the present invention without the addition of the above-mentioned activator, a problem arises in that the catalyst is deteriorated in a short period of time, thereby disadvantageously leading to a lowering of the yield of the desired (meth)acrylonitrile.

In the present invention, it is preferred that the silica carrier is present in an amount of from 10 to 60 by weight, based on the total weight of the compound oxide and the silica carrier, and that the compound oxide is represented by the following formula (1):

$$Mo_1Te_aV_bNb_cX_dO_n \qquad (1)$$

wherein:

X is at least one element selected from the group consisting of tantalum, tungsten, chromium, titanium, zirconium, antimony, bismuth, tin, hafnium, manganese, iron, ruthenium, cobalt, rhodium, nickel, palladium, platinum, zinc, aluminum, gallium, indium, thallium, phosphorus and alkaline earth metals; and a, b, c, d and n are, respectively, the atomic ratios of tellurium, vanadium, niobium, X and oxygen, relative to molybdenum, wherein $$0.01 \leq a < 1.0,$$

more advantageously $0.05 \leq a \leq 0.5$;

$$0.1 \leq b < 1.0;$$

more advantageously $0.2 \leq b < 0.6$;

$$0.01 \leq c \leq 1.0;$$

more advantageously $0.05 \leq c \leq 0.5$;
$0 \leq d \leq 1.0$;
more advantageously $0 \leq d < 0.1$;
and n is a number determined by and consistent with the valence requirements of the other elements present in the compound oxide of formula (1).

Further, when the addition of the activator is conducted in an ammoxidation using a catalyst other than the catalyst defined in the present invention, the above-mentioned excellent effects cannot be obtained. Examples of catalysts other than the catalyst defined in the present invention include an oxide catalyst containing only Mo and Te as active component elements, an oxide catalyst containing only Mo, Te and Cr as active component elements and an oxide catalyst containing only V, Sb and Te as active component elements.

The activator used in the process of the present invention comprises at least one tellurium compound and optionally at least one molybdenum compound. The molybdenum compound is optionally used as an auxiliary activator. When the molybdenum compound is used as an auxiliary activator, the molybdenum compound may be added to the reactor separately from the tellurium compound, or may be added to the reactor together with the tellurium compound.

In the present invention, it is preferred to use a tellurium compound which can be converted into an oxide of tellurium under the conditions for the ammoxidation of propane or isobutane. Specific examples of tellurium compounds include metallic tellurium; inorganic tellurium compounds, such as telluric acid, tellurium dioxide and tellurium trioxide; and organic tellurium compounds, such as methyltellurol and dimethyl telluroxide. Among these, telluric acid is preferred.

In the present invention, when the molybdenum compound is used in the activator, it is preferred to use a molybdenum compound which can be converted into an oxide of molybdenum under the conditions for the ammoxidation of propane or isobutane. Specific examples of molybdenum compounds include ammonium heptamolybdate, molybdic acid, molybdenum dioxide and molybdenum trioxide. Among these, ammonium heptamolybdate is preferred.

It is preferred that the activator is not in a carrier-supported form for the following reason. For example, when a silica-supported tellurium dioxide is used as the activator, such an activator is difficult to maintain the ability to reactivate a deteriorated catalyst for a prolonged period of time, and, therefore, it becomes difficult to stably perform the production of (meth)acrylonitrile for a prolonged period of time while maintaining a high yield of (meth)acrylonitrile.

In the present invention, there is no particular limitation with respect to the method for adding the activator into the fluidized-bed reactor. As an example of the method for adding the activator into the reactor, there can be mentioned a method using a reactor having connected thereto a pipe for the activator, which is provided separately from a pipe for a feed-stock gas. In this method, the activator in a powder form can be introduced into the reactor through the pipe for the activator, together with gas, such as air or nitrogen gas. In this instance, when the activator is introduced into the dense phase of the reactor (in which the catalyst is present in a high concentration), it becomes possible for the activator to be mixed with the catalyst sufficiently to achieve a good contact between the activator and the catalyst.

In the present invention, the addition of the activator may be conducted in a continuous manner or in a batchwise manner.

With respect to the time period needed for achieving a satisfactory reactivation of the catalyst after the addition of the activator, such a time period is generally from 2 to 10 hours.

With respect to the frequency of the addition of the activator and the amount of the activator added to the reactor, there is no particular limitation. For example, the frequency and the amount can be appropriately determined by a simple method in which the activator is portionwise added to the reactor while monitoring the results of the ammoxidation.

In the process of the present invention, the frequency of the addition of the activator is not particularly limited, as long as the effects of the present invention can be obtained. However, for example, when the process of the present invention is practiced on a commercial scale, it is preferred that the addition of the activator is made at a frequency of once in 1 to 30 days, more advantageously once in 1 to 7 days.

In the process of the present invention, it is preferred that the amount of a tellurium compound added as the activator into the reactor at one time is 20% by weight or less, more advantageously 10% by weight or less, in terms of the amount of tellurium atom, based on the original weight of the tellurium atom contained in the catalyst.

In the process of the present invention, when the at least one molybdenum compound is added as an optional activator, it is preferred that the amount of the molybdenum compound added into the reactor at one time is 10% by weight or less, more advantageously 5% by weight or less, in terms of the amount of molybdenum atom, based on the original weight of the molybdenum atom contained in the catalyst.

The addition of a molybdenum compound as a part of the activator may be made when, for example, the occurrence of a loss of molybdenum from the catalyst is detected. A loss of molybdenum from the catalyst can be detected by, for example, subjecting a sample of the catalyst to X-ray fluororescence analysis.

With respect to the mechanism of the deterioration of a catalyst based on a compound oxide containing tellurium, complete elucidation has not yet been made. Generally, when production of acrylonitrile or methacrylonitrile by ammoxidation of propane or isobutane is performed in the presence of a tellurium-containing oxide catalyst, the tellurium contained in the catalyst continues to be gradually lost with a lapse of time during the course of the reaction, and the yield of the desired unsaturated nitrile also continues to lower in accordance with the loss of tellurium from the catalyst. However, in such ammoxidation, it has occasionally been observed that, in the initial stage of the ammoxidation, the yield of acrylonitrile or methacrylonitrile rather increases, irrespective of the fact that the tellurium content of the catalyst decreases with a lapse of time. Therefore, the lowering of the yield of acrylonitrile or methacrylonitrile in ammoxidation using a tellurium-containing oxide catalyst cannot be simply explained by the loss of tellurium from the catalyst.

With respect to the mechanism by which the activator used in the process of the present invention restores or maintains the catalytic activity of a catalyst comprising a compound oxide containing molybdenum, tellurium, vanadium and niobium, complete elucidation has not yet been made. It is conceivable that, during the course of the ammoxidation using a fluidized-bed reactor containing a catalyst comprising a compound oxide containing molybdenum, tellurium, vanadium and niobium, the activator (which is generally used in a particulate form) interacts with the compound oxide at outer surfaces or at interior portions of particles of the compound oxide (wherein the interior portions of the compound oxide particles can be contacted by, for example, the vapor from of the activator), so that the interactions between the activator and the compound oxide particles brings about a repairing effect on the damaged crystal structure of the compound oxide which has suffered a reductive degradation specific to the type of the catalyst used in the process of the present invention.

In fact, when experiments are performed in which the process of the present invention is practiced, and an X-ray diffraction pattern of the catalyst is measured before and after the addition of the activator, and a comparison is made between these X-ray diffraction patterns of the catalyst, the comparison sometimes shows that a damaged portion of the crystal structure of the catalyst has been repaired to some extent. However, in many cases, no significant differences are observed between these X-ray diffraction patterns of the catalyst, irrespective of the fact the catalytic activity of the catalyst is surely restored by the addition of the activator. Therefore, the catalyst activation mechanism involved in the process of the present invention cannot be explained by referring to only a repair of the crystal-structural damage which can be observed by X-ray diffractometry.

Hereafter, the method for producing the catalyst used in the process of the present invention is described.

With respect to the source of each component element for the compound oxide of the ammoxidation catalyst used in the process of the present invention, there is no particular limitation. Representative examples of sources of component elements for the compound oxide of the catalyst include ammonium heptamolybdate $[(NH_4)_6Mo_7O_{24} \cdot 4H_2O]$ as a source of molybdenum; telluric acid $(H_6TeO_6)$ as a source of tellurium; ammonium metavanadate $(NH_4VO_3)$ as a source of vanadium; and niobic acid $(Nb_2O_5 \cdot nH_2O)$ as a source of niobium.

Examples of sources of other component elements for the compound oxide of the catalyst used in the process of the present invention include nitrates, oxalates, acetates, hydroxides, oxides, ammonium salts and carbonates of elements, such as tantalum, tungsten, chromium, titanium, zirconium, antimony, bismuth, tin, hafnium, manganese, iron, ruthenium, cobalt, rhodium, nickel, palladium, platinum, zinc, aluminum, gallium, indium, thallium, phosphorus and alkaline earth metals.

With respect to the source of silica as a carrier for the compound oxide of the catalyst, a silica sol is preferred.

The catalyst used in the process of the present invention can be produced by a conventional method. For example, the catalyst can be produced by a method comprising the steps of (1) preparing a raw material mixture (for example, a slurry of raw materials), (2) drying the raw material mixture obtained in step (1) above to obtain a dried catalyst precursor, and (3) subjecting the dried catalyst precursor obtained in step (2) above to calcination.

Hereinbelow, explanation is made with respect to a preferred embodiment of the above-mentioned method for producing the catalyst used in the process of the present invention, which comprises steps (1), (2) and (3) above.

In step (1), a raw material mixture is prepared. For this purpose, a solution is first prepared by dissolving ammonium heptamolybdate, telluric acid and ammonium metavanadate in water (this solution is designated "solution A").

On the other hand, oxalic acid and niobic acid are dissolved in water to obtain a solution (this solution is designated "solution B").

As mentioned above, the compound oxide of the catalyst used in the process of the present invention optionally contains at least one component element selected from the group consisting of the following elements: tantalum, tungsten, chromium, titanium, zirconium, antimony, bismuth, tin, hafnium, manganese, iron, ruthenium, cobalt, rhodium, nickel, palladium, platinum, zinc, aluminum, gallium, indium, thallium, phosphorus and alkaline earth metals. A nitrate, an oxalate, an acetate, a hydroxide, an oxide, an ammonium salt, a carbonate or the like of the above-mentioned at least one component element is dissolved in water, to obtain a solution or slurry (this solution or slurry is designated "solution C").

To solution A are successively added solution B, solution C and a silica sol, to thereby obtain a raw material mixture. The order of the addition of solution B, solution C and the silica sol can be appropriately changed.

In step (2), the raw material mixture obtained in step (1) above is subjected to spray drying. The spray drying of the raw material mixture can be generally conducted by centrifugation, two-phase flow nozzle method or high pressure nozzle method to obtain a dried spherical particulate catalyst precursor. In this instance, it is preferred to use air which has been heated by an electric heater, steam or the like, as a heat source for drying. It is preferred that the temperature of the spray dryer at an entrance to the dryer section thereof is from 150 to 300° C.

It is preferred that the spray drying is performed under conditions such that the oxide catalyst obtained after calcination in step (3) below has a particle diameter of 5 to 120 $\mu$m, and an average particle diameter of about 50 $\mu$m.

In step (3), the dried particulate catalyst precursor obtained in step (2) above is calcined. The calcination of the dried particulate catalyst is conducted in an atmosphere of an inert gas, such as nitrogen gas, argon gas or helium gas, which is substantially free of oxygen, preferably under a flow of an inert gas, at a temperature of 500 to 700° C., preferably 550 to 650° C. for 0.5 to 20 hours, preferably 1 to 8 hours, thereby obtaining an oxide catalyst.

For the calcination, use can be made of a kiln, such as a rotary kiln, a tunnel kiln, a muffle kiln and a fluidized firing kiln.

Prior to the calcination in step (3), the dried catalyst precursor obtained in step (2) above may be heat-treated in an atmosphere of air or under a stream of air at a temperature of 200° to 400° C. for 1 to 5 hours.

In the process of the present invention, using a fluidized-bed reactor, acrylonitrile or methacrylonitrile is produced by the gaseous phase ammoxidation of propane or isobutane in the presence of the above-obtained oxide catalyst.

Propane or isobutane and ammonia used in the process of the present invention need not be of very high purity but may be of a commercial grade.

Examples of sources of molecular oxygen include air, an oxygen-rich air and pure oxygen. Further, such a source of molecular oxygen may be diluted with helium, argon, nitrogen, carbon dioxide, steam or the like.

In the process of the present invention, the catalytic ammoxidation of propane or isobutane in the gaseous phase can be conducted under the following conditions. The [propane or isobutane:ammonia molecular oxygen] molar ratio is generally in the range of from 1:0.3 to 1.5:0.5 to 10, preferably from 1:0.8 to 1.2:1 to 5. The ammoxidation temperature is generally in the range of from 350° to 500 ° C., preferably from 380° to 470 ° C. The ammoxidation pressure is generally in the range of from 0.5 to 5 atm., preferably from 1 to 3 atm. The time of contact (contact time) between the gaseous feedstocks and the catalyst is generally in the range of from 0.1 to 10 sec.g/cc, preferably from 0.5 to 5 sec·g/cc.

In the process of the present invention, the contact time during the catalytic ammoxidation of propane or isobutane is determined according to the following formula:

Contact time (sec·g/cc)=

$$(W/F) \times \frac{273}{(273+T)}$$

wherein:
W represents the weight (g) of the catalyst contained in the fluidized-bed reactor;
F represents the flow rate (Ncc/sec) of the gaseous feedstocks [Ncc means cc as measured under the normal temperature and pressure conditions (0° C., 1 atm)]; and
T represents the reaction temperature (°C).

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, an ammoxidation of propane was conducted to produce acrylonitrile.

The results of the ammoxidation were evaluated in terms of the conversion (%) of propane, the selectivity (%) for acrylonitrile and the yield (%) of acrylonitrile, which are, respectively, defined as follows:

$$\text{Conversion (\%) of propane} = \frac{\text{mole of propane reacted}}{\text{mole of propane fed}} \times 100$$

Selectivity (%) for acrylonitrile =

$$\frac{\text{mole of acrylonitrile formed}}{\text{mole of propane reacted}} \times 100$$

$$\text{Yield of acrylonitrile (\%)} = \frac{\text{mole of acrylonitrile formed}}{\text{mole of propane fed}} \times 100$$

EXAMPLE 1

Preparation of an ammoxidation catalyst

An oxide catalyst comprising a silica carrier having supported thereon a compound oxide, wherein the silica carrier is present in an amount of 25% by weight in terms of $SiO_2$, based on the total weight of the compound oxide and the silica carrier, and wherein the compound oxide is represented by the formula: $MO_1Te_{0.23}V_{0.3}Nb_{0.11}O_n$ was prepared as follows.

To 4840 g of water were added 1173.9 g of ammonium heptamolybdate [$(NH_4)_6Mo_7O_{24}\cdot 4H_2O$], 352.2 g of telluric acid ($H_6TeO_6$) and 241.9 g of ammonium metavanadate ($NH_4VO_3$), while stirring at about 60° C., to thereby obtain an aqueous solution (solution A).

To 1190 g of water were added 126.0 g of niobic acid ($Nb_2O_5$ content: 76.6% by weight) and 274.7 g of oxalic acid ($H_2C_2O_4\cdot 2H_2O$), while stirring at about 60° C., to thereby obtain an aqueous solution (solution B).

To solution A obtained above were added solution B obtained above and 1667 g of silica sol having an $SiO_2$ content of 30% by weight, while stirring, to thereby obtain a raw material mixture.

The obtained raw material mixture was subjected to spray drying by means of a centrifugation type spray-drying apparatus under conditions such that the entrance and exit temperatures were 240° C. and 145° C., respectively, to thereby obtain a dried particulate catalyst precursor.

The obtained catalyst precursor was heat-treated in the air at 250° C. for 2 hours to obtain a compound oxide. 700 g of the obtained compound oxide was charged into a SUS tube (diameter: 2 inch) and calcined at 600° C. for 2 hours under a stream of nitrogen gas at a flow rate of 600 Ncc/min (Ncc means cc as measured under the normal temperature and pressure conditions, namely, at 0° C. under 1 atm.), to thereby obtain an oxide catalyst. The calcination of another 700 g of the oxide compound was conducted in substantially the same manner as mentioned above, to thereby prepare an oxide catalyst in an amount sufficient for use in the desired ammoxidation.

Ammoxidation of propane 800 g of the oxide catalyst prepared above was charged into a fluidized-bed SUS reaction tube (inner diameter: 82 mm) having 12 wire nets (16 mesh) provided therein and arranged in a perpendicular relationship to the inner vertical wall of the reaction tube and in parallel to each other, wherein each of the distances between adjacent wire nets was 1 cm. A gaseous mixture having a molar ratio of propane:ammonia:air of 1:1.2:14 was fed into the reaction tube from a lower portion thereof at a flow rate of 104 Ncc/sec, to thereby effect an ammoxidation of propane to produce acrylonitrile. The ammoxidation temperature was 430° C. and the ammoxidation pressure was atmospheric. The time of contact (contact time) between the oxide catalyst and the gaseous mixture of the feedstocks was 3.0 sec·g/cc.

About 2 hours after the start of the ammoxidation, the results of the ammoxidation were evaluated, and it was found that the conversion of propane was 86.5%, the selectivity for acrylonitrile was 60.5%, and the yield of acrylonitrile was 52.3%. The results of the ammoxidation were also evaluated 2 days and 6 days after the start of the reaction, and the obtained results are shown in Table 1.

Then, as an activator, telluric acid ($H_6TeO_6$) in a powder form was portionwise added into the reaction tube as follows.

7 Days after the start of the ammoxidation, 10 g of a first portion of the telluric acid was introduced into the reaction tube through a pipe connected thereto for the activator, together with a flow of nitrogen gas. About 2 hours after the addition of the telluric acid, the results of the ammoxidation were evaluated, and it was found that the results of the ammoxidation were improved, as compared to those evaluated 6 days after the start of the ammoxidation (i.e., one day before the addition of the telluric acid). 5 Hours after the addition of the telluric acid, the results of the ammoxidation were evaluated, and it was found that the conversion of propane was 86.8%, the selectivity for acrylonitrile was 60.5%, and the yield of acrylonitrile was 52.5%.

Further, a second portion (8 g), a third portion (6 g), a fourth portion (7 g) and a fifth portion (7 g) of telluric acid were, respectively, added into the reaction tube 15, 20, 26 and 32 days after the start of the ammoxidation in substantially the same manner as mentioned above. During this period, the yield of acrylonitrile maintained a level of from 50 to 53%.

38 Days after the start of the reaction, another activator which was in a powder form and which had been obtained by mixing 6 g of telluric acid ($H_6TeO_6$) and 10 g of ammonium heptamolybdate [$(NH_4)_6Mo_7O_{24} \cdot 4H_2O$] was added into the reaction tube in substantially the same manner as mentioned above. The results of the ammoxidation were evaluated 40 days after the start of the ammoxidation, and it was found that the conversion of propane was 87.0%, the selectivity for acrylonitrile was 60.2%, and the yield of acrylonitrile was 52.4%.

The amounts of the activators added into the reaction tube, and the results of the ammoxidation evaluated 2 hours, 2, 6, 7 and 40 days after the start of the ammoxidation are shown in Table 1.

TABLE 1

| Time after the start of ammoxidation | Activator (g) | | Ammoxidation of propane | | |
|---|---|---|---|---|---|
| | Telluric acid | Ammonium heptamolybdate | Conversion (%) | Selectivity (%) | Yield (%) |
| 2 hours | 0 | 0 | 86.5 | 60.5 | 52.3 |
| 2 days | 0 | 0 | 87.4 | 60.3 | 52.7 |
| 6 days | 0 | 0 | 89.3 | 54.3 | 48.5 |
| 7 days | 10 | 0 | 86.8 | 60.5 | 52.5 |

TABLE 1-continued

| Time after the start of ammoxidation | Activator (g) | | Ammoxidation of propane | | |
|---|---|---|---|---|---|
| | Telluric acid | Ammonium heptamolybdate | Conversion (%) | Selectivity (%) | Yield (%) |
| 15 days | 8 | 0 | — | — | — |
| 20 days | 6 | 0 | — | — | — |
| 26 days | 7 | 0 | — | — | — |
| 32 days | 7 | 0 | — | — | — |
| 38 days | 6 | 10 | — | — | — |
| 40 days | 0 | 0 | 87.0 | 60.2 | 52.4 |

Example 2

Ammoxidation of propane under stringent reaction conditions

An ammoxidation of propane was performed using the catalyst prepared in Example 1 in a manner as described below to observe the deterioration and reactivation of the catalyst.

45 g of the catalyst prepared in Example 1 was charged into a fluidized-bed Vycor-glass reaction tube (inner diameter: 25 mm) having 8 wire nets (16 mesh) provided therein and arranged in a perpendicular relationship to the inner vertical wall of the reaction tube and in parallel to each other, wherein each of the distances between adjacent wire nets was 1 cm. A gaseous mixture having a molar ratio of propane ammonia : air of 1:1.2:14 was fed into the reaction tube from a lower portion thereof at a flow rate of 5.83 Ncc/sec, to thereby effect an ammoxidation of propane to produce acrylonitrile. The ammoxidation temperature was 430° C. and the ammoxidation pressure was atmospheric. The time of contact (contact time) between the catalyst and the gaseous mixture of the feedstocks was 3.0 sec·g/cc.

About 2 hours after the start of the ammoxidation, the results of the ammoxidation were evaluated, and it was found that the conversion of propane was 87.1%, the selectivity for acrylonitrile was 60.3%, and the yield of acrylonitrile was 52.5%.

About 5 hours after the start of the ammoxidation, the ammoxidation temperature was elevated from 430° C. to 490° C. Under the stringent reaction conditions (ammoxidation temperature=490° C.), the ammoxidation was continued for about 10 hours, and then, the ammoxidation temperature was returned to 430 ° C. Subsequently, the results of the ammoxidation were evaluated, and it was found that the conversion of propane was 60.3%, the selectivity for acrylonitrile was 44.2% and the yield of acrylonitrile was 26.7%.

Then, telluric acid ($H_6TeO_6$) was portionwise added into the reaction tube as follows. 1.0 g of a first portion of the telluric acid was added into the reaction tube in the same manner as in Example 1. About 2 hours after the addition of the first portion of the telluric acid, the results of the ammoxidation were evaluated, and it was found that the conversion of propane was 80.1%, the selectivity for acrylonitrile was 53.2% and the yield of acrylonitrile was 42.6%. This indicates that the results of the ammoxidation were improved after the addition of the first portion of telluric acid, as compared to those evaluated after the ammoxidation under the stringent reaction conditions and before the addition of the first portion of the telluric acid. 0.7 g of a second portion of the telluric acid and 0.3 g of a third portion of the telluric acid were, respectively, added into the reaction tube 7 hours and 12 hours after the addition of the first portion of the telluric acid. 17 Hours after the addition of the first portion of the telluric acid, the results of the ammoxidation were evaluated. As a result, it was found that the conversion of propane was 88.5 %, the selectivity for acrylonitrile was 58.9%, and the yield of acrylonitrile was 52.1%.

The results of Example 2 are shown in Tables 2 and 3.

Comparative Example 1

Preparation of an ammoxidation catalyst

An oxide catalyst mentioned in Example 12 of U.S. Pat. No. 4,709,070, wherein the oxide catalyst is represented by the formula: $Fe_{10}Sb_{25}W_{0.25}Te_{1.0}O_{67.8}(SiO_2)_{30}$, was prepared as follows.

To 700 g of water was added 636.5 g of ferric nitrate [$Fe(NO_3)_3 \cdot 9H_2O$], while stirring, to thereby obtain an aqueous solution (solution A).

To 350 g of water were added 10.2 g of ammonium paratungstate [$(NH_4)_{10}W_{12}O_{41} \cdot 5H_2O$] and 36.2 g of telluric acid ($H_6TeO_6$), while stirring at about 95° C., to thereby obtain an aqueous solution (solution B).

To solution A obtained above were added solution B obtained above, 568.9 g of diantimony trioxide ($Sb_2O_3$) powder and 937 g of silica sol having an $SiO_2$ content of 30% by weight, while stirring, followed by addition of aqueous ammonia ($NH_3$ content: 15% by weight) until the pH value of the resultant mixture became 2, to thereby obtain a raw material mixture.

The obtained raw material mixture was subjected to spray drying under substantially the same conditions as in Example 1, to thereby obtain a dried particulate catalyst precursor.

The obtained catalyst precursor was subjected to calcination in the air at 500° C. for 4 hours, and then, at 850° C. for 1 hour, to thereby obtain a catalyst.

Ammoxidation of propane under stringent reaction conditions

An ammoxidation of propane was performed using the catalyst prepared above in a manner as described below to observe the deterioration and reactivation of the catalyst.

Using 45 g of the catalyst prepared above, an ammoxidation was performed in substantially the same manner as in Example 2, except that the ammoxidation temperature was 500° C. and the contact time was 5.0 sec-g/cc.

About 2 hours after the start of the ammoxidation, the results of the ammoxidation were evaluated, and it was found that the conversion of propane was 31.4%, the selectivity for acrylonitrile was 27.4% and the yield of acrylonitrile was 8.6%.

About 5 hours after the start of the ammoxidation, the ammoxidation temperature was elevated from 500° C. to 550° C. Under the stringent reaction conditions (ammoxidation temperature=550° C.), the ammoxidation was continued for about 10 hours, and then, the ammoxidation temperature was returned to 500° C. Subsequently, the results of the ammoxidation were evaluated, and it was found that the conversion of propane was 23.2%, the selectivity for acrylonitrile was 18.0% and the yield of acrylonitrile was 4.2%.

Then, telluric acid ($H_6TeO_6$) was portionwise added into the reaction tube as follows. 0.3 g of a first portion of the telluric acid was added into the reaction tube. About 5 hours after the addition of the first portion of the telluric acid, the results of the ammoxidation were evaluated, and it was found that the conversion of propane was 25.0%, the selectivity for acrylonitrile was 16.8% and the yield of acrylonitrile was 4.2%.

About 10 hours after the addition of the first portion of the telluric acid, 0.2 g of a second portion of the telluric acid was added into the reaction tube, and the subsequent ammoxidation was monitored so as to determine whether or not an improvement can be achieved in the results of the ammoxidation. As a result, it was found that no improvement was obtained in the results of the ammoxidation.

The results of Comparative Example 1 are shown in Tables 2 and 3.

Comparative Example 2

Preparation of an ammoxidation catalyst

An oxide catalyst mentioned in Example 13 of U.S. Pat. No. 4,709,070, wherein the oxide catalyst is represented by the formula:

$Fe_{10}Sb_{25}Cu_3Mo_{0.5}W_{0.3}Te_{1.5}O_{73.4}(SiO_2)_{60}$, was prepared as follows.

To 520 g of water were added 468.9 g of ferric nitrate [$Fe(NO_3)_3 \cdot 9H_2O$], and 84.1 g of copper(II) nitrate [$Cu(NO_3)_2 \cdot 3H_2O$], while stirring, to thereby obtain an aqueous solution (solution A).

To 300 g of water were added 10.2 g of ammonium heptamolybdate [$(NH_4)_6Mo_7O_{24} \cdot 4H_2O$], 9.0 g of ammonium paratungstate [$(NH_4)_{10}W_{12}O_{41} 5H_2O$] and 40.0 g of telluric acid ($H_6TeO_6$), while stirring at about 95° C., to thereby obtain an aqueous solution (solution B).

To solution A obtained above were added solution B, 419.1 g of diantimony trioxide ($Sb_2O_3$) powder and 1,381 g of silica sol having an $SiO_2$ content of 30% by weight, while stirring, followed by addition of aqueous ammonia ($NH_3$ content: 15% by weight) until the pH value of the resultant mixture became 2, to thereby obtain a raw material mixture.

The obtained raw material mixture was subjected to spray drying under substantially the same conditions as in Example 1, to thereby obtain a dried particulate catalyst precursor.

The obtained catalyst precursor was subjected to calcination in the air at 500° C. for 4 hours, and then, at 850° C. for 1 hour, to thereby obtain a catalyst.

Ammoxidation of propane under stringent reaction conditions

An ammoxidation of propane was performed using the catalyst prepared above in a manner as described below to observe the deterioration and reactivation of the catalyst.

Using 45 g of the catalyst prepared above, an ammoxidation was performed in substantially the same manner as in Example 2, except that the ammoxidation temperature was 500° C. and the contact time was 5.0 sec·g/cc.

About 2 hours after the start of the ammoxidation, the results of the ammoxidation were evaluated, and it was found that the conversion of propane was 32.0%, the selectivity for acrylonitrile was 28.3% and the yield of acrylonitrile was 9.1%.

About 5 hours after the start of the ammoxidation, the ammoxidation temperature was elevated from 500° C. to 550° C. Under the stringent reaction conditions (ammoxidation temperature=550° C.), the ammoxidation was continued for about 10 hours, and then, the ammoxidation temperature was returned to 500° C. Subsequently, the results of the ammoxidation were evaluated, and it was found that the conversion of propane was 24.1%, the selectivity for acrylonitrile was 21.2% and the yield of acrylonitrile was 5.1%.

Then, telluric acid ($H_6TeO_6$) was portionwise added into the reaction tube as follows. 0.3 g of a first portion of the telluric acid was added into a reaction tube. About 5 hours after the addition of the first portion of the telluric acid, the results of the ammoxidation were evaluated, and it was found that the conversion of propane was 25.8%, the selectivity for acrylonitrile was 19.4% and the yield of acrylonitrile was 5.0%.

About 10 hours after the addition of the first portion of the telluric acid, 0.2 g of a second portion of the telluric acid was added into the reaction tube, and the subsequent ammoxidation was monitored so as to determine whether or not an improvement can be achieved in the results of the ammoxidation. As a result, it was found that no improvement was obtained in the results of the ammoxidation.

The results of Comparative Example 2 are shown in Tables 2 and 3.

Comparative Example 3

Preparation of an ammoxidation catalyst

A catalyst composition comprising a silica carrier having supported thereon an oxide catalyst, wherein the silica carrier is present in an amount of 20% by weight, based on the total weight of the silica carrier and the oxide catalyst and wherein the oxide catalyst comprises a compound oxide described in Example 4 of Unexamined Japanese Patent Application Laid-Open Specification No. 7-215926 and represented by the formula: $Mo_1Te_{0.5}Al_{8.0}O_n$, was prepared as follows.

To 2,200 g of water were added 222.3 g of ammonium heptamolybdate [$(NH_4)_6Mo_7O_{24} \cdot 4H_2O$] and 145.0 g of telluric acid ($H_6TeO_6$), while stirring at 60° C., to thereby obtain an aqueous solution (solution A).

To 1,100 g of water was added 3,752.2 g of aluminum nitrate [$Al(NO_3)_3 \cdot 9H_2O$], while stirring at about 60° C., to thereby obtain an aqueous solution (solution B).

To solution A obtained above were added 667 g of silica sol having an $SiO_2$ content of 30% by weight and solution B obtained above, while stirring, to thereby obtain a raw material mixture.

The obtained raw material mixture was subjected to spray drying under substantially the same conditions as in Example 1, to thereby obtain a dried particulate catalyst precursor.

The obtained catalyst precursor was subjected to calcination in the air at 65° C. for 3 hours, to thereby obtain a catalyst.

Ammoxidation of propane under stringent reaction conditions

An ammoxidation of propane was performed using the catalyst prepared above in a manner as described below to observe the deterioration and reactivation of the catalyst.

Using 45 g of the catalyst prepared above, an ammoxidation was performed in substantially the same manner as those in Example 2, except that the ammoxidation temperature was 50° C. and the contact time was 7.6 sec-g/cc.

About 2 hours after the start of the ammoxidation, the results of the ammoxidation were evaluated, and it was found that the conversion of propane was 77.6%, the selectivity for acrylonitrile was 37.9% and the yield of acrylonitrile was 29.4%.

About 5 hours after the start of the ammoxidation, the ammoxidation temperature was elevated from 500° C. to 550° C. Under the stringent reaction conditions (ammoxidation temperature =550° C.), the ammoxidation was continued for about 10 hours, and then, the ammoxidation temperature was returned to 500° C. Subsequently, the results of the ammoxidation were evaluated, and it was found that the conversion of propane was 54.0%, the selectivity for acrylonitrile was 22.8% and the yield of acrylonitrile was 12.3%.

Then, telluric acid ($H_6TeO_6$) was portionwise added into the reaction tube as follows. 1.0 g of a first portion of the telluric acid was added into the reaction tube. About 5 hours after the addition of the first portion of the telluric acid, the results of the ammoxidation were evaluated, and it was found that the conversion of propane was 56.2%, the selectivity of acrylonitrile was 22.2% and the yield of acrylonitrile was 12.5%.

About 10 hours after the addition of the first portion of the telluric acid, 0.7 g of a second portion of the telluric acid was added into the reaction tube, and the subsequent ammoxidation was monitored so as to determine whether or not an improvement can be achieved in the results of the ammoxidation. As a result, it was found that no improvement was obtained in the results of the ammoxidation.

The results of Comparative Example 3 are shown in Tables 2 and 3.

Comparative Example 4

Preparation of an ammoxidation catalyst

An oxide catalyst mentioned in Example 1 of U.S. Pat. No. 5,171,876, comprising silica and alumina carriers having supported thereon a compound oxide, wherein the silica carrier is present in an amount of 25% by weight in terms of $SiO_2$, and the alumina carrier is present in an amount of 25% by weight in terms of $Al_2O_3$, each based on the total weight of the compound oxide, and the silica carrier and the alumina carrier, and wherein the oxide catalyst is represented by the formula: $Mo_1Te_{0.5}Cr_{0.5}Mg_{0.5}O_n$, was prepared as follows.

To 3,100 g of water were added 306.6 g of ammonium heptamolybdate [$(NH_4)_6Mo_7O_{24}$]$4H_2O$ and 199.9 g of telluric acid ($H_6TeO_6$), while stirring at 60° C., to thereby obtain an aqueous solution (solution A).

To 1,500 g of water were added 345.4 g of chromium nitrate [$Cr(NO_3)_3 \cdot 9H_2O$] and 222.8 g of magnesium nitrate [$Mg(NO_3)_2 \cdot 6H_2O$], while stirring at about 60° C., to thereby obtain an aqueous solution (solution B).

To solution A obtained above were added solution B obtained above, 833 g of silica sol ($SiO_2$ content: 30% by weight) and 1,250 g of alumina sol ($Al_2O_3$ content: 20% by weight), while stirring, to thereby obtain a raw material mixture.

The obtained raw material mixture was subjected to spray drying under substantially the same conditions as in Example 1, to thereby obtain a dried particulate catalyst precursor.

The obtained catalyst precursor was subjected to calcination in the air at 290° C. for 3 hours, and then, at 425° C. for 3 hours, and finally at 610° C. for 3 hours, to thereby obtain a catalyst.

Ammoxidation of propane under stringent reaction conditions

An ammoxidation of propane was performed using the catalyst prepared above in a manner as described below to observe the deterioration and reactivation of the catalyst.

Using 45 g of the catalyst prepared above, an ammoxidation was performed in substantially the same manner as in Example 2, except that the ammoxidation temperature was 470° C.

About 2 hours after the start of the ammoxidation, the results of the ammoxidation were evaluated, and it was found that the conversion of propane was 15.0%, the selectivity for acrylonitrile was 60.2% and the yield of acrylonitrile was 9.0%.

About 5 hours after the start of the ammoxidation, the ammoxidation temperature was elevated from 470° C. to 520° C. Under the stringent reaction conditions (ammoxidation temperature =520° C.), the ammoxidation was continued for about 10 hours, and then, the ammoxidation temperature was returned to 470° C. Subsequently, the results of the ammoxidation were evaluated, and it was found that the conversion of propane was 12.5%, the selectivity for acrylonitrile was 28.8% and the yield of acrylonitrile was 3.6%.

Then, telluric acid ($H_6TeO_6$) was portionwise added into the reaction tube as follows. 1.4 g of a first portion of the telluric acid was added into the reaction tube. About 5 hours after the addition of the first portion of the telluric acid, the results of the ammoxidation were evaluated, and it was found that the conversion of propane was 14.0%, the selectivity for acrylonitrile was 25.1% and the yield of acrylonitrile was 3.5%.

About 10 hours after the addition of the first portion of the telluric acid, 0.7 g of a second portion of the telluric acid was added into the reaction tube, and the subsequent ammoxidation was monitored so as to determine whether or not an improvement can be achieved in the results of the ammoxidation. As a result it was found that no improvement was obtained in the results of the ammoxidation.

The results of Comparative Example 4 are shown in Tables 2 and 3.

Comparative Example 5

Preparation of an ammoxidation catalyst

A catalyst composition comprising a silica carrier having supported thereon an oxide catalyst, wherein the silica carrier is present in an amount of 25% by weight, based on the total weight of the silica carrier and the oxide catalyst and wherein the oxide catalyst comprises a compound oxide described in Example 1 of Unexamined Japanese Patent Application Laid-Open Specification No. 6-228073 and represented by the formula: $W_1V_{0.3}TeO_{0.23}Nb_{0.12}O_n$, was prepared as follows.

To 4,000 g of water were added 311.5 g of ammonium paratungstate [$(NH_4)_{10}W_{12}O_{41} \cdot 5H_2O$], 63.4 g of telluric acid ($H_6TeO_6$), 42.1 g of ammonium metavanadate ($NH_4VO_3$), while stirring at 95° C., to thereby obtain an aqueous solution (solution A).

To 240 g of water were 24.8 g of niobic acid ($Nb_2O_5$ content: 76.6% by weight) and 54.0 g of oxalic acid ($H_2C_2O_4 19\ 2H_2O$), while stirring at about 60° C., to thereby obtain an aqueous solution (solution B).

To solution A obtained above were added 417 g of silica sol having an $SiO_2$ content of 30% by weight and solution B, while stirring, to thereby obtain a raw material mixture.

The obtained raw material mixture was subjected to spray drying under substantially the same conditions as in Example 1, to thereby obtain a dried particulate catalyst precursor.

80 g of the obtained catalyst precursor was charged into a SUS tube (inner diameter: 1 inch) and calcined at 600° C. for 2 hours under a stream of nitrogen gas at a flow rate of 150 Ncc/min, to thereby obtain a catalyst.

Ammoxidation of propane under stringent reaction conditions

An ammoxidation of propane was performed using the catalyst prepared above in a manner as described below to observe the deterioration and reactivation of the catalyst.

Using 45 g of the catalyst prepared above, an ammoxidation was performed in substantially the same manner as in Example 2, except that the ammoxidation temperature was 450° C.

About 2 hours after the start of the ammoxidation, the results of the ammoxidation were evaluated, and it was found that the conversion of propane was 65.3%, the selectivity for acrylonitrile was 21.0% and the yield of acrylonitrile was 13.7%.

About 5 hours after the start of the ammoxidation, the ammoxidation temperature was elevated from 450° C. to 500° C. Under the stringent reaction conditions (ammoxidation temperature=500° C.), the ammoxidation was continued for about 10 hours, and then, the ammoxidation temperature was returned to 450° C. Subsequently, the results of the ammoxidation were evaluated, and it was found that the conversion of propane was 36.6%, the selectivity for acrylonitrile was 18.6% and the yield of acrylonitrile was 6.8%.

Then, telluric acid ($H_6TeO_6$) was portionwise added into the reaction tube as follows. 0.8 g of a first portion of the telluric acid was added into the reaction tube. About 5 hours after the addition of the first portion of the telluric acid, the results of the ammoxidation were evaluated, and it was found that the conversion of propane was 37.0%, the selectivity for acrylonitrile was 17.6% and the yield of acrylonitrile 6.5%.

About 10 hours after the addition of the first portion of the telluric acid, 0.5 g of a second portion of the telluric acid was added into the reaction tube, and the subsequent ammoxidation was monitored so as to determine whether or not an improvement can be achieved in the results of the ammoxidation. As a result it was found that no improvement was obtained in the results of the ammoxidation.

The results of Comparative Example 5 are shown in Tables 2 and 3.

TABLE 2

| Catalyst | | Reaction temperature (° C.) | Temperature for stringent reaction conditions (° C.) | Amount of activator (telluric acid) added (g) |
|---|---|---|---|---|
| Ex. 2 | $Mo_1Te_{0.23}V_{0.31}Nb_{0.11}O_n/25$ wt % $SiO_2$ | 430 | 490 | 1.0 + 0.7 + 0.3 |
| Comp. Ex. 1 | $Fe_{10}Sb_{25}W_{0.25}Te_{1.0}O_{67.8}(SiO_2)_{30}$ | 500 | 550 | 0.3 (+0.2) |
| Comp. Ex. 2 | $Fe_{10}Sb_{25}Cu_3Mo_{0.5}W_{0.3}Te_{1.5}O_{73.4}(SiO_2)_{60}$ | 500 | 550 | 0.3 (+0.2) |
| Comp. Ex. 3 | $Mo_1Te_{0.5}Al_{8.0}O_n/20$ wt % $SiO_2$ | 500 | 550 | 1.0 (+0.7) |
| Comp. Ex. 4 | $Mo_1Te_{0.5}Cr_{0.6}Mg_{0.5}O_n/(25$ wt % $SiO_2$ + 25 wt % $Al_2O_3)$ | 470 | 520 | 1.4 (+0.7) |
| Comp. Ex. 5 | $W_1V_{0.3}Te_{0.23}Nb_{0.12}O_n/25$ wt % $SiO_2$ | 450 | 500 | 0.8 (+0.5) |

TABLE 3

| | Results obtained 2 hours after the start of reaction | | | Results obtained after applying stringent reaction conditions | | | Results obtained after the addition of activator | | |
|---|---|---|---|---|---|---|---|---|---|
| | Conversion (%) | Selectivity (%) | Yield (%) | Conversion (%) | Selectivity (%) | Yield (%) | Conversion (%) | Selectivity (%) | Yield (%) |
| Ex. 2 | 87.1 | 60.3 | 52.5 | 60.3 | 44.2 | 26.7 | 88.5 | 58.9 | 52.1 |
| Comp. Ex. 1 | 31.4 | 27.4 | 8.6 | 23.2 | 18.0 | 4.2 | 25.0 | 16.8 | 4.2 |
| Comp. Ex. 2 | 32.0 | 28.3 | 9.1 | 24.1 | 21.2 | 5.1 | 25.8 | 19.4 | 5.0 |
| Comp. Ex. 3 | 77.6 | 37.9 | 29.4 | 54.0 | 22.8 | 12.3 | 56.2 | 22.2 | 12.5 |
| Comp. Ex. 4 | 15.0 | 60.2 | 9.0 | 12.5 | 28.8 | 3.6 | 14.0 | 25.1 | 3.5 |
| Comp. Ex. 5 | 65.3 | 21.0 | 13.7 | 36.6 | 18.6 | 6.8 | 37.0 | 17.6 | 6.5 |

INDUSTRIAL APPLICABILITY

As described above, in the process of the present invention, acrylonitrile or methacrylonitrile is produced from propane or isobutane by a gaseous phase ammoxidation of propane or isobutane in a fluidized-bed reactor containing a catalyst comprising a compound oxide containing molybdenum (Mo), tellurium (Te), vanadium (V) and niobium (Nb), wherein the reaction is performed with an addition of a catalyst activator comprising a tellurium compound and optionally a molybdenum compound into the reactor. The process of the present invention is advantageous in that the catalytic activity of the catalyst is surely maintained at a high level even without replacing the catalyst with a fresh one by interrupting the ammoxidation reaction, so that production of acrylonitrile or methacrylonitrile by the ammoxidation of propane or isobutane can be stably performed for a prolonged period of time while maintaining a high yield of acrylonitrile or methacrylonitrile.

What is claimed is:

1. A process for producing acrylonitrile or methacrylonitrile from propane or isobutane by ammoxidation, which comprises:

reacting propane or isobutane with ammonia and molecular oxygen in the gaseous phase in a fluidized-bed reactor containing a catalyst comprising a compound oxide and a silica carrier having supported thereon said compound oxide, said compound oxide containing molybdenum (Mo), tellurium (Te), vanadium (V) and niobium (Nb), wherein said reaction is performed with an addition of an activator for said catalyst into said reactor, said activator comprising at least one tellurium compound and optionally at least one molybdenum compound.

2. The process according to claim 1, wherein said silica carrier is present in an amount of from 10 to 60% by weight, based on the total weight of said compound oxide and said silica carrier, and wherein said compound oxide is represented by the following formula (1):

$$Mo_1Te_aV_bNb_cX_dO_n \quad (1)$$

wherein:

X is at least one element selected from the group consisting of tantalum, tungsten, chromium, titanium, zirconium, antimony, bismuth, tin, hafnium, manganese, iron, ruthenium, cobalt, rhodium, nickel, palladium, platinum, zinc, aluminum, gallium, indium, thallium, phosphorus and alkaline earth metals; and a, b, c, d and n are, respectively, the atomic ratios of tellurium, vanadium, niobium, X and oxygen, relative to molybdenum, wherein $0.01 \leq a < 1.0$;

$0.1 \leq b \leq 1.0$;

$0.01 \leq c \leq 1.0$;

$0 < d \leq 1.0$; and n is a number determined by and consistent with the valence requirements of the other elements present in the compound oxide of formula (1).

3. The process according to claim 1 or 2, wherein said at least one tellurium compound is selected from the group consisting of metallic tellurium, an inorganic tellurium compound and an organic tellurium compound, and said at least one molybdenum compound is selected from the group consisting of ammonium heptamolybdate, molybdic acid, molybdenum dioxide and molybdenum trioxide.

4. The process according to claim 3, wherein said inorganic tellurium compound is at least one member selected from the group consisting of telluric acid, tellurium dioxide and tellurium trioxide, and said organic tellurium compound is at least one member selected from the group consisting of methyltellurol and dimethyl telluroxide.

5. The process according to claim 1 or 2, wherein said at least one tellurium compound is telluric acid and said at least one molybdenum compound is ammonium heptamolybdate.

* * * * *

UNITED STATES PATENT AND TRADEMARK OFFICE
CERTIFICATE OF CORRECTION

PATENT NO. : 5,907,052
APPLICATION NO. : 09/132224
DATED : May 25, 1999
INVENTOR(S) : Kazuyuki Hamada et al.

It is certified that error appears in the above-identified patent and that said Letters Patent is hereby corrected as shown below:

Column 5, line 24
The formula reading "$0.01 \leq a < 1.0$" should read -- $0.01 \leq a \leq 1.0$ --

Column 5, line 28
The formula reading "$0.01 \leq b < 1.0$" should read -- $0.01 \leq b \leq 1.0$ --

Column 5, line 31
The formula reading "$0.2 \leq b < 0.6$" should read -- $0.2 \leq b \leq 0.6$ --

Column 5, line 37
The formula reading "$0 \leq d < 0.1$" should read -- $0 \leq d \leq 0.1$ --.

Column 18, line 3
The formula "$H_2C_2O_4 19\ 2H_2O$" should read -- $H_2C_2O_4 \cdot 2H_2O$ --

Column 20, line 41
The formula reading "$0.01 \leq a < 1.0$" should read -- $0.01 \leq a \leq 1.0$ --

Column 20, line 43
The formula reading "$0.01 \leq c\ 1.0$" should read -- $0.01 \leq c \leq 1.0$ --;

Column 20, line 44
The formula reading "$0 < d \leq 1.0$" should read -- $0 \leq d \leq 1.0$ --.

Signed and Sealed this

Twenty-second Day of August, 2006

JON W. DUDAS
*Director of the United States Patent and Trademark Office*